United States Patent
Pike (10) Patent No.: US 6,889,831 B2
(45) Date of Patent: May 10, 2005

(54) BIN

(75) Inventor: Gregory C. Pike, Clayton (AU)

(73) Assignee: Sharp Products International Pty. Ltd., Ormond (AU)

( * ) Notice: Subject to any disclaimer, the term of this patent is extended or adjusted under 35 U.S.C. 154(b) by 254 days.

(21) Appl. No.: 10/212,145

(22) Filed: Aug. 6, 2002

(65) Prior Publication Data

US 2003/0168367 A1 Sep. 11, 2003

Related U.S. Application Data

(60) Provisional application No. 60/361,325, filed on Mar. 5, 2002.

(51) Int. Cl.[7] .............................................. B65D 85/24
(52) U.S. Cl. ...................................... 206/366; 206/370
(58) Field of Search ............................... 206/63.5, 366, 206/370, 438; 220/229, 908, 910; 232/44, 47, 62

(56) References Cited

U.S. PATENT DOCUMENTS

| | | | | |
|---|---|---|---|---|
| 524,637 A | * | 8/1894 | Johnson | ........................ 232/24 |
| 1,135,264 A | * | 4/1915 | Cox | |
| 4,969,554 A | * | 11/1990 | Sawaya | ........................ 206/370 |
| 5,080,251 A | * | 1/1992 | Noack | ........................ 206/366 |
| 5,560,512 A | * | 10/1996 | Hahn | ........................ 220/810 |
| 5,630,506 A | * | 5/1997 | Thorne et al. | .............. 206/366 |
| 6,283,909 B1 | * | 9/2001 | Sharp | ........................ 588/258 |

* cited by examiner

Primary Examiner—David T. Fidei
(74) Attorney, Agent, or Firm—Stites & Harbison PLLC; Ross F. Hunt, Jr.

(57) ABSTRACT

A closure member for a bin having an enclosure with a closed end and a mouth, the closure member being adapted to be secured to or to form part of the mouth of the bin and comprising two blade assemblies mounted to be rotatable and to extend across the mouth of the bin, means to urge each blade assembly to rotate to an operative position, each blade assembly comprising at least one blade, the blade assemblies being arranged so that adjacent blades of each assembly are vertically offset and overlap to define, in the operative position, a vertical gap between the adjacent blades.

23 Claims, 7 Drawing Sheets

BIN

CROSS REFERENCE TO RELATED APPLICATIONS

This application claims benefit of U.S. Provisional Application No. 60/361,325, filed on Mar. 5, 2002.

FIELD OF THE INVENTION

This invention relates to a bin and more particularly to a closure member for the mouth of a bin.

BACKGROUND OF THE INVENTION

In the medical industries there is a frequent need for bins in which can be placed—bandages, needles, wrapping and many of the other waste products that are generated in hospitals, doctor's surgeries or other medical practices. Some of the contents of bins of this kind can be extremely hazardous and great care has to be taken that the users of such bins do not come into contact with the material that is being placed in the bins. There is thus a need to provide a bin that provides ready access for a variety of different types of materials. There is also a need for a bin that has a closure member that restricts access of a user's hand with simple hands free means of opening the closure member to provide ready access to the interior of the bin without direct contact with the bin.

SUMMARY OF THE INVENTION

It is the needs described above that have brought about the present invention which whilst primarily directed at bins for use in the medical industry is understood to cover bins for use in many other environments.

In accordance with one aspect of the present invention there is provided a closure member for a bin having an enclosure with a closed end and a mouth, the closure member being adapted to be secured to or to form part of the mouth of the bin and comprising two blade assemblies mounted to be rotatable and to extend across the mouth of the bin, means to urge each blade assembly to rotate to an operative position, each blade assembly comprising at least one blade, the blade assemblies being arranged so that adjacent blades of each assembly are vertically offset and overlap to define, in the operative position, a vertical gap between the adjacent blades.

In one embodiment, each blade assembly is unbalanced by offsetting the point about which the blade assembly rotates from the centre of gravity of the blade assembly thereby biasing the blade assembly towards the operative position.

Where means is used to urge the blade into the operative position the blade does not necessarily have to be mounted in an unbalanced configuration and even if the blade is unbalanced it is not the imbalance that causes the rotation to the operative position but the means, usually a spring, that urges the blade into that configuration.

In one embodiment each blade assembly comprises a spindle with three blades extending radially from the spindle at substantially equal angular spacing.

In another embodiment the blades are of differing shape and length so that when the blade assembly is supported in the mouth of the bin about the spindle the assembly is unbalanced to rotate to the operative position.

Thus in this embodiment the unbalanced nature of the blade assemblies is caused by the difference in geometry of the blades. In another embodiment the blades have the same geometry but a counterbalance weight is placed on at least one blade to unbalance the assembly. This counterweight may be adjustable to ensure correct rotation and positioning of the blade assemblies during operation.

In a preferred embodiment each blade assembly is placed in parallel spaced apart across the mouth of the bin with the axis of one assembly being vertically displaced from the axis of the other assembly.

Preferably the bin defines a stop for each blade assembly against which a blade abuts due to the unbalanced nature of the assembly to assume the operative position. When in the operative position adjacent blades of the assemblies overlap in a vertical sense to define a gap between the assemblies in a vertical plane. The adjacent blades, when in the operative position, are preferably downwardly inclined.

The present invention also embraces a bin that incorporates a closure member of the kind described above. It is further understood that in a preferred embodiment that a cover may be placed over the frame to close off the bin for transportation.

BRIEF DESCRIPTION OF THE DRAWINGS

Embodiments of the present invention will now be described by way of example only with reference to the accompanying drawings in which:

FIG. 4 is a cross-sectional view of the bin and closure member in an operative position;

DESCRIPTION OF THE PREFERRED EMBODIMENTS

A first embodiment of a medical waste bin assembly 10 is shown in FIGS. 1 to 6. The bin assembly 10 essentially comprises a bin 20, a frame 30 arranged to support two blade assemblies 40 and 41 with a cover 50 that seals off the bin. The cover 50 clips onto the top of the bin 20 to seal the assembly for transportation and is removed during use and is thus not shown in the other views. The invention essentially relates to a closure member in the form of the frame 30 and blade assemblies 40, 41 although it is understood that the invention also embraces a bin incorporating the closure member and cover.

Figure 1:
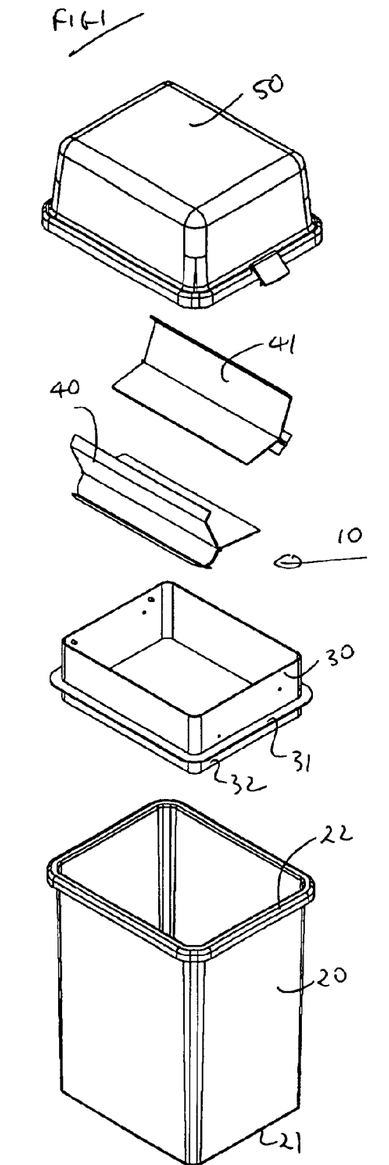
FIG. 1 is an exploded perspective view of a medical waste bin assembly incorporating a closure member according to a first embodiment of the present invention.
Figure 2:
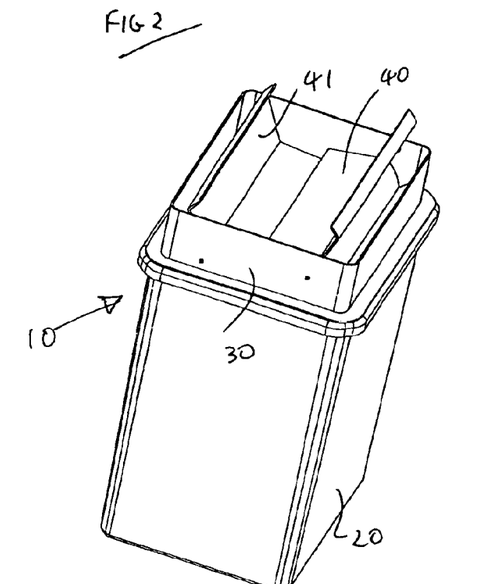
FIG. 2 is a perspective view of the bin assembly supporting the closure member in accordance with the first embodiment of the invention.
Figure 3:
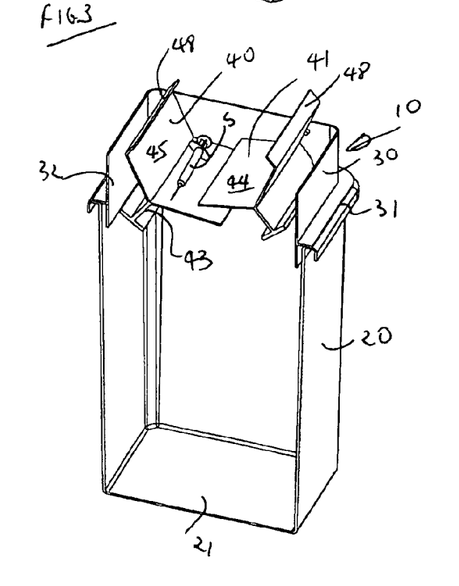
FIG. 3 is a cut away perspective view of the bin and closure member.
Figure 5:
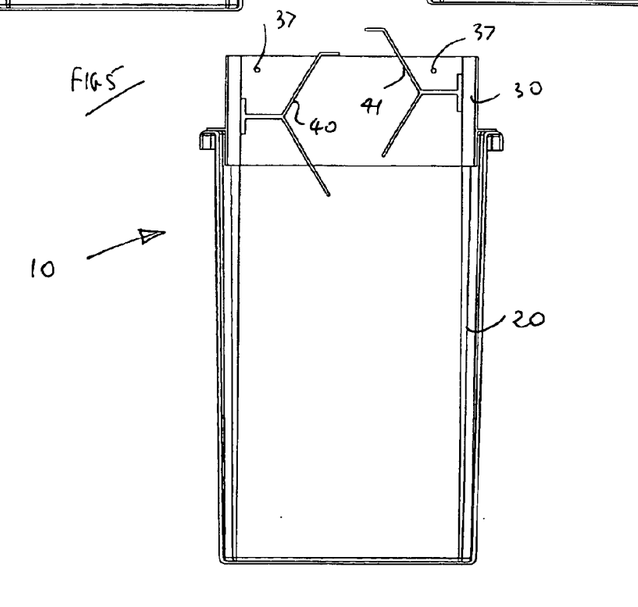
FIG. 5 is a cross-sectional view of the bin and closure member in a partially open position.

The bin 20 is of rectangular configuration defining an enclosure with a closed end 21 and an open mouth 22. It is however understood that the bin can assume many other shapes. The frame 30 has an outwardly extending peripheral skirt 31 which sits on the top of the mouth 22 of the bin with a downwardly projecting rim 32 that sits flush within the interior of the bin as shown in FIG. 3. It is however understood that the blade assemblies could be attached to the upper part of the bin in a manner that the frame 30 becomes an integral component of the bin.

Each blade assembly 40, 41 comprises three blades 43, 44, 45 extending radially from an apex at approximately equal angular spacings, namely angularly spaced at 120°. As shown in FIGS. 3 and 4 each blade is differently shaped with the first blade 43 comprising a short radial flange 46 with a mutually perpendicular T piece 47 at the radial end. The second blade 44 is a longer rectangular blade and the third blade 45 is also substantially rectangular but with an inturned flange 48 on its free end. The second blade assembly 41 is virtually the same as the first blade assembly except that the longer rectangular blade 44 in the second blade assembly is shorter in radial projection. As shown in FIG. 3, the blade assemblies are mounted with their axes parallel but the second blade assembly 41 is vertically above the first blade assembly 40. The frame 30 on which the blade assemblies is mounted is an elongate rectangular member open at both ends with the blade assemblies mounted substantially within, but not totally within, the member as shown in the drawings.

The facts that the blades of each blade assembly are of different shape and their orientation means that the blade assembly is not balanced causing the assembly to rotate so the heaviest blade rotates towards the base of the bin until the assembly hits a stop 37. The frame 30 is provided with the stop 37 that projects inwardly from one wall 32 to act as an abutment that restrains the blade assembly from further rotation and causes it to resume the operative position shown in FIGS. 3 and 4. As can be seen in FIG. 4, when the blade assemblies 40, 41 are in the operative position resting against the stops 37, the blades 44 of each assembly 40, 41 extend laterally across the mouth of the opening. Their elongate shape means that they substantially fill the opening to define no gap when viewed from the top. There is however, due to the offset mounting of the blade assemblies 40, 41, a vertical gap 60 between the two blades 44 that overlap as shown in FIG. 4.

Although the unbalanced nature of the blade assemblies is due to the blades differing shapes and orientation it is understood that blades of identical shapes could be used together appropriately positioned weights that provide the degree of instability to cause the blade assemblies 40, 41 to rotate to the operative position against the stops 37.

Figures 6, 7:
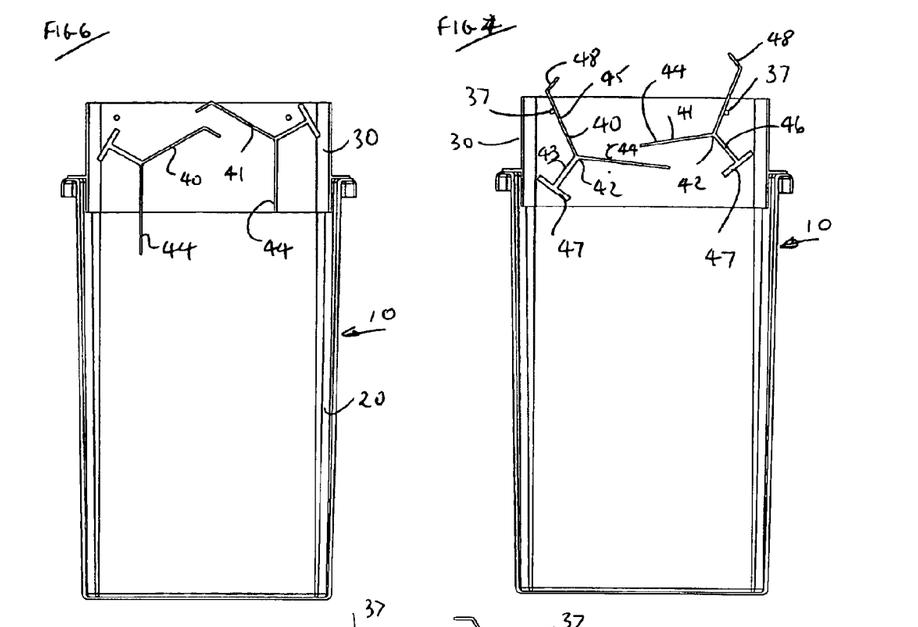
FIG. 6 is a cross-sectional view of the bin and closure member in a fully open position.
FIG. 7 is an exploded perspective view of a medical waste bin assembly according to a second embodiment of the invention.
Figure 7:
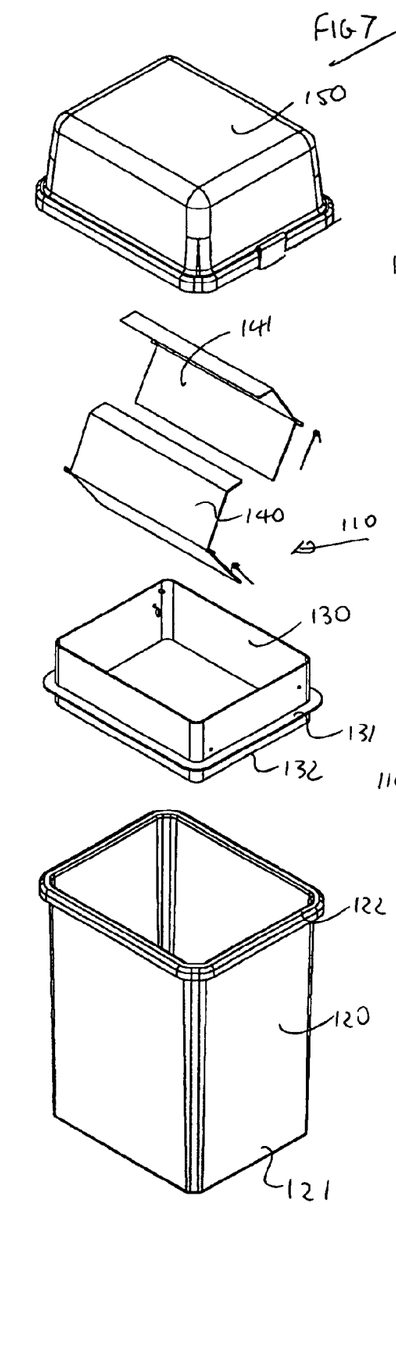
Figure 8:
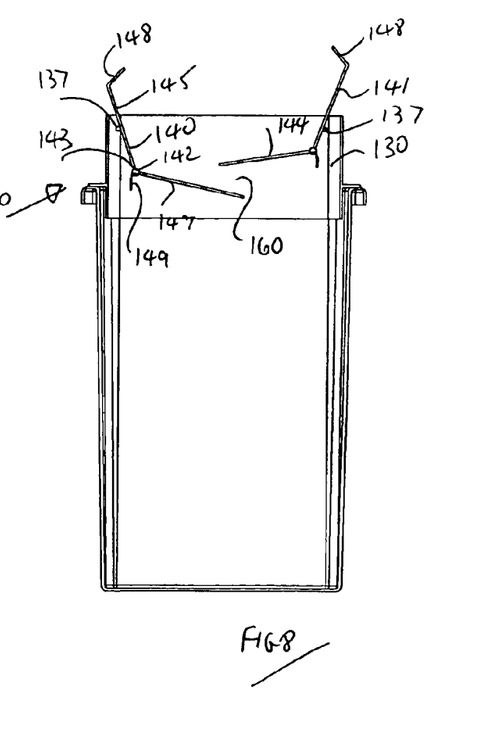
FIG. 8 is a cross-sectional view of the bin and closure member of FIG. 7 in an operative position.
Figure 9:
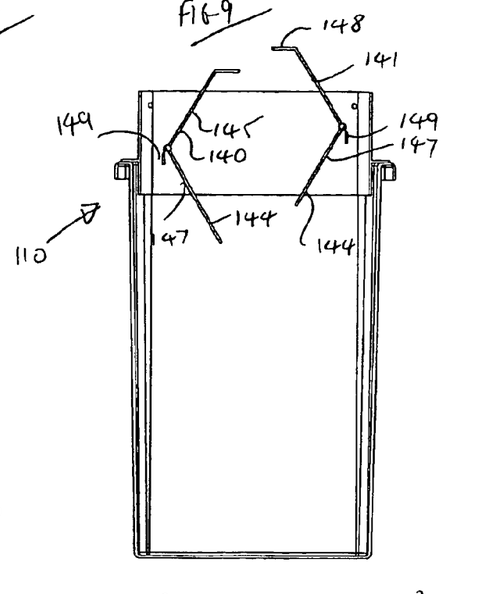
FIG. 9 is a cross-sectional view of the bin and closure member of FIG. 7 in a partially open position.
Figure 10:
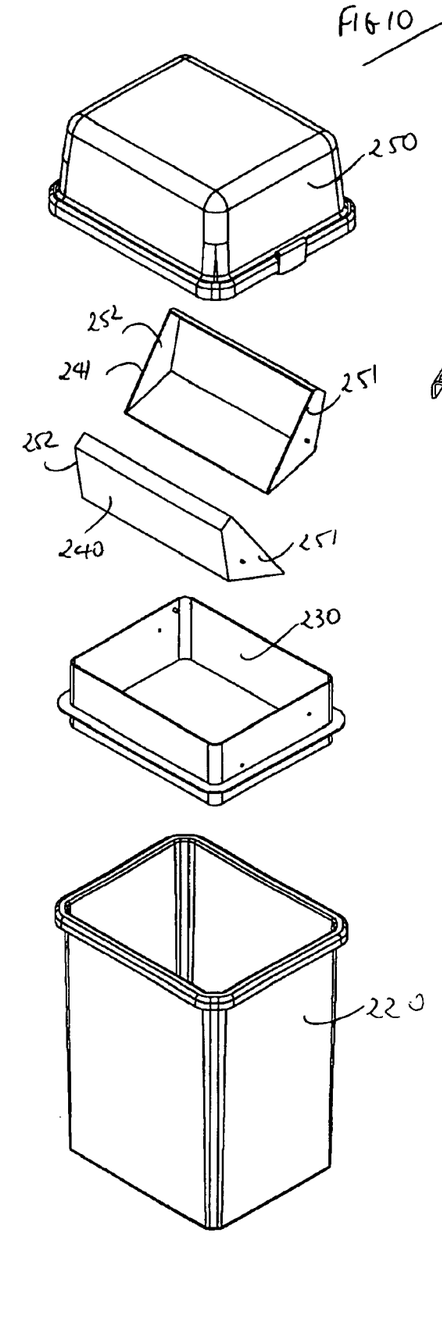
FIG. 10 is an exploded perspective view of a medical waste bin assembly incorporating a closure member according to a third embodiment of the present invention.

A second embodiment of a medical waste bin assembly 110 is shown in FIGS. 7 to 9. Similar to the first embodiment, the bin assembly 110 essentially comprises a bin 120, a frame 130 arranged to support two blade assemblies 140 and 141 with a cover 150 that seals off the bin.

In this embodiment, each blade assembly 140, 141 comprises an elongate central spindle 142 with two blades 144, 145 extending radially therefrom angularly spaced at about 120°. As shown in FIG. 8 each blade is differently shaped with the first blade 144 being a rectangular blade and the second blade 145 having an inturned flange 148 on its free end. The blade assemblies 140, 141 are mounted with their axes parallel but the second blade assembly 141 is vertically above the first blade assembly 140.

The spindle 142 of each blade is attached to a small coil spring 143 that has an arm 147 that extends under the blade 144 and a second arm 149 that locates against the frame 130 so that the spring 143 urges the blade assembly upwardly to the position shown in FIG. 4, namely the operative position.

The remaining features of the second embodiment illustrated in FIGS. 7 to 9 are similar to the first embodiment including that the frame 130 is provided with a stop 137, the blade assemblies 140, 141 resting against the stops 137 when in the operative position. When in the operative position, the blades 144 of each assembly 140, 141 extend laterally across the mouth of the opening. When viewed from the top there is no gap between the blades however the offset mounting of the blade assemblies provides a vertical gap 160 between the overlapping blades 144 as illustrated in FIG. 8.

FIGS. 10 to 13 illustrate a third embodiment of the invention that operates in a substantially similar manner as the first two embodiments, and particularly the first embodiment, with the difference lying in the cause of imbalance in the blade assemblies. Specifically, in the first embodiment the blade assemblies are unbalanced as a result of the shape and orientation of the assemblies, namely the heavier, blade rotating the blade assembly towards the operative position. In the third embodiment the blade assemblies 241, 240 only comprise two blades 244, 245 extending radially from an elongate vertex 242. The blades are spaced at about 120°, with one blade longer than the other and the other blade having internal flange 248. Essentially, the blade assembly construction is similar to that in the second embodiment, but, additionally in the third embodiment, the blade assemblies also comprise end flanges 251, 252 to define surfaces from which each blade can be pivoted. The end flanges 251, 252 also serve to improve the containment capacity i.e. fully contain any waste positioned within the opening of the blade assembly.

Figure 11:
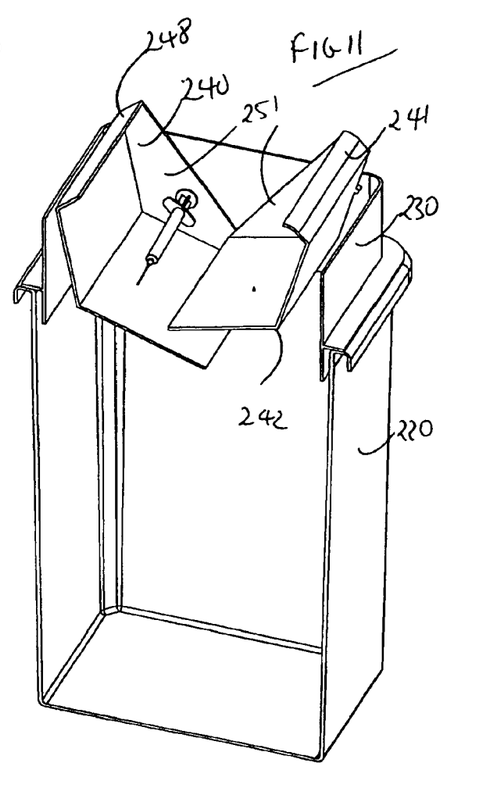
FIG. 11 is a cut-away perspective view of the bin and closure member of the third embodiment.
Figures 12, 13:
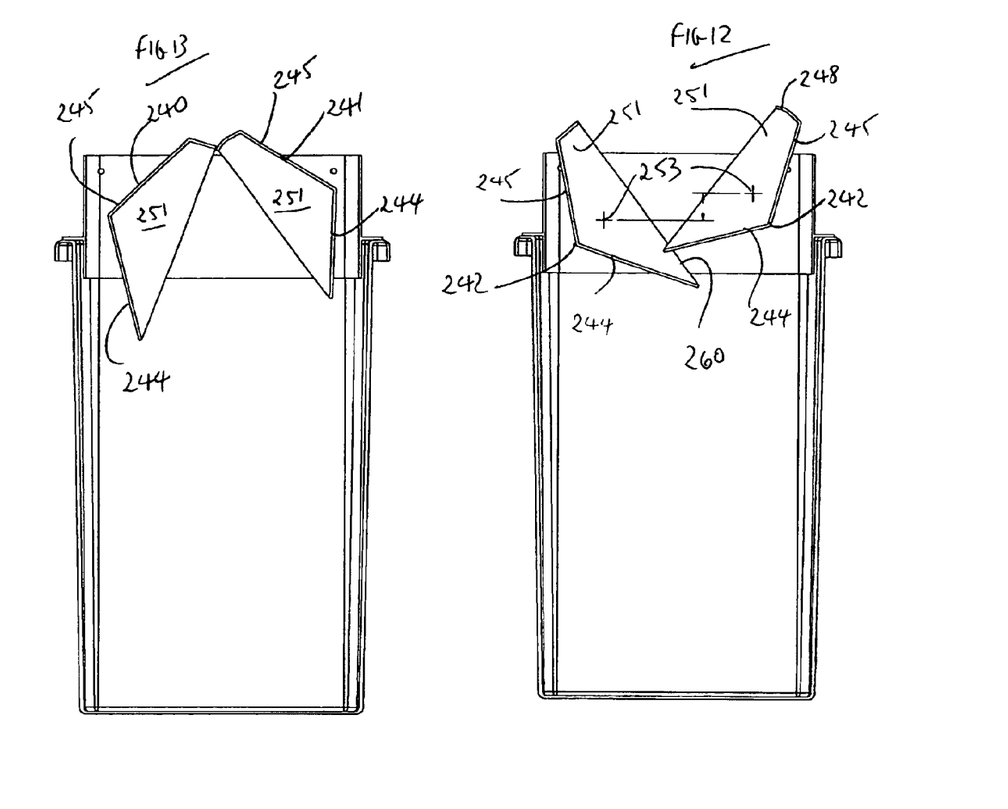
FIG. 12 is a cross-sectional view of the bin and closure member of FIG. 11 in an operative position.
FIG. 13 is a cross-sectional of the bin and closure member of FIG. 11 in a fully opened position.
Figure 14:
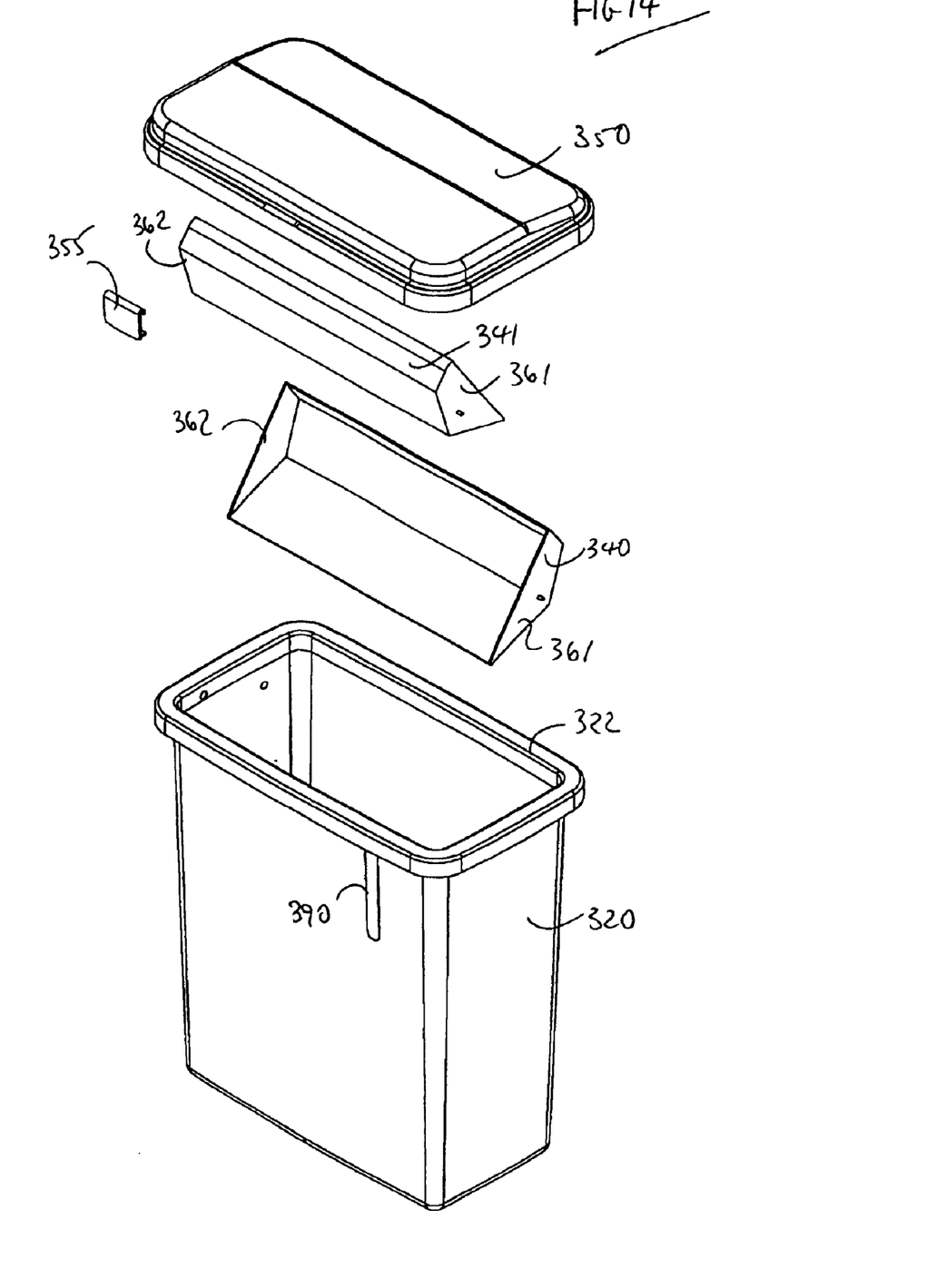
FIG. 14 is an exploded view of a waste bin assembly according to a fourth embodiment of the invention.
Figure 15:
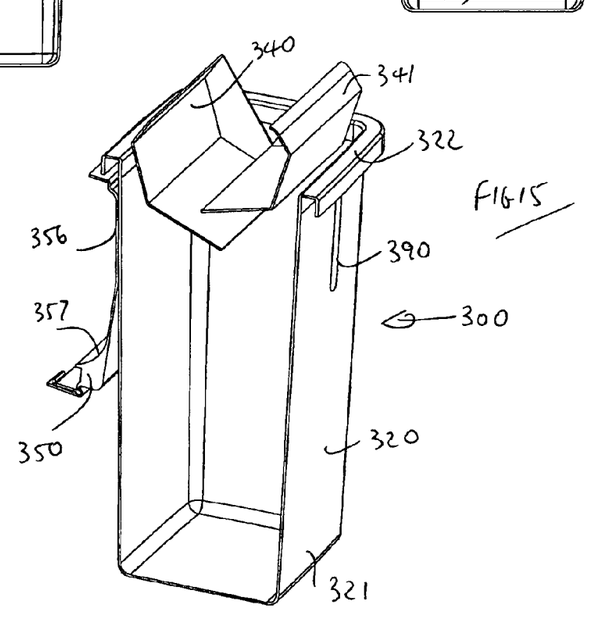
FIG. 15 is a perspective view of the bin with the front cut-away showing the blade assemblies in an operative position.

The blade assemblies of the third embodiment are biased into the operative position by unbalancing the blade assemblies. This is achieved by moving the point of rotation of the assemblies from the central spindle 42, 142 of the previous embodiments to a pivot point 253 illustrated in FIG. 12 that is higher and more inward of the vertex 242. Important to this embodiment, when viewed in cross-section as in FIG. 12, pivot point 253 is offset from the point of centre of gravity in the blade assemblies thereby urging the blade assemblies into the operative position as illustrated in FIGS. 11 and 12. Therefore, rather than relying on a longer, heavier blade to unbalance the blade assemblies as in the first embodiment, the pivot point offset from the centre of gravity causes the rotation. Thus, the blades can assume a variety of shapes and weights whilst still functioning as described. Firstly, the centre of gravity is found. This is the axis about which the blades will freely rotate in balance and its position will depend on the length, weight and other characteristics of the blades. The pivot point is then offset from the centre of gravity in a direction that will cause the desirable rotation of the blade assemblies. With one assembly it was found a 0.5 mm displacement of the pivot point from the centre of gravity provided suitable blade assembly rotation. The degree and sensitivity of blade assembly rotation may be adjusted by finely shifting the position of the pivot point relative to the centre of gravity. Furthermore, owing to the offset mounting of the blade assemblies 240, 241, a vertical gap 260 exists between the two overlapping blades 244 in the operative position as illustrated in FIG. 12.

In the fourth embodiment shown in FIGS. 14 to 17 the blade assemblies 340 and 341 are mounted directly to the upper portion of the bin 320 that has a peripheral outwardly extending rim 322. The blade assemblies 340 and 341 are substantially the same as the blade assemblies shown in the third embodiment with end flanges 361, 362 that define eccentrically mounted pivot points that cause the blade assemblies to freely pivot into the operative position shown in FIG. 15.

Figure 16:
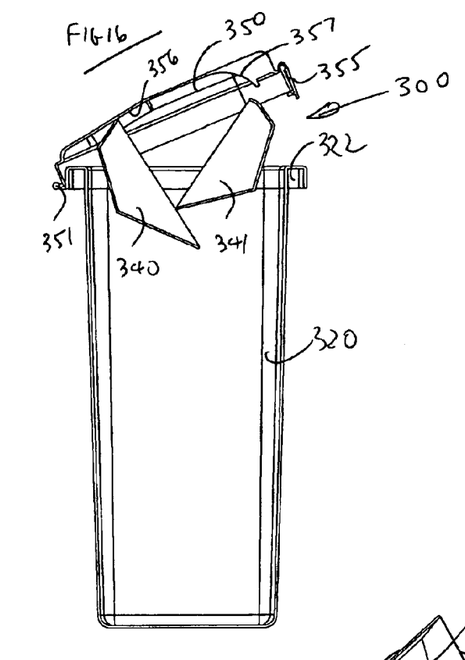
FIG. 16 is a cross-section view of the bin assembly with a cover partially closed.
Figure 17:
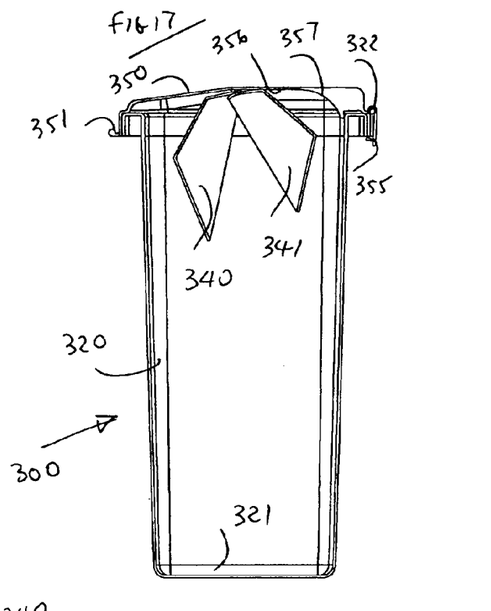
FIG. 17 is a cross-sectional view of the assembly with the cover closed.

In this embodiment the bin has a cover 350 secured on one side via a hinge 351. The cover 350 has an underside 356 that includes a camming portion 357 that terminates in its forward edge with a latch 355 that is adapted to clip against the rim 322 to close the bin for transportation as shown in FIG. 17. FIG. 16 shows the closing action of the cover with the underside 356 and camming surface 357 having the effect of causing the blade assemblies 340 and 341 to be rotated into the transportation position as shown in FIG. 17 in which the bulk of the blade assemblies is below the level of the top of the bin and the cover 350 can assume the closed and locked configuration shown in FIG. 17. The cover 350 is designed to orientate the blade assemblies so that it can be closed without a hand having to touch the blade assemblies. This improves the safety features of the bin assembly.

Whilst in this embodiment the blade assemblies are eccentrically mounted as in the third embodiment, it is understood that the blade assemblies could be mounted in the same manner as the blade assemblies of earlier embodiments. This embodiment also includes the provision of an elongate viewing window 390 in the wall of the bin 320. This viewing window provides a ready indication of when the bin is full and it provides viewing access to the bin at a level just below the blade assemblies.

Thus in the operative position of all embodiments the contents of the bin are closed off by the blade assemblies 40, 41, 140, 141, 240, 241, 340, 341. When an item for disposal such as a syringe, as shown in FIGS. 3 and 11, is placed in the opening of the blade assemblies it falls against either one of the blades 44, 144, 244 causing blade assembly 40, 140, 240, 340 to rotate in a clockwise direction to the position shown in FIGS. 5, 9 and 13 thereby defining a horizontal gap through which the syringes fall into the interior of the bin. The rotation of the blade assembly 40, 140, 240, 340 is such that the blade 44, 144, 244 is at a particularly steep angle to the horizontal ensuring that the syringes or even lighter material would slide off its surface into the bin. However, very small and light articles may fall onto the blade assemblies but do not cause their rotation. In this case the downwardly inclined surface 44, 144, 244 of the blade assemblies in the operative position shown in FIGS. 4, 8, 12 and 15 ensures that these light articles slide off the blade assemblies to drop into the container. When heavier and larger items are placed on the blade assemblies they both turn to rotate to the position shown in FIGS. 5, 9 and 13 to thereby define a tortuous path from the exterior to the interior of the bin through which an operator's hand is restricted. Internal flanges 48, 148, 248 contribute to restrict access to the interior of the bin by an operator's hand. This discourages the user from placing his/her hand into the bin. FIGS. 6, 9 and 13 show the vertically and open positions in which both of the blades 44, 144, 244 extend downwards to define a very large horizontal opening. This allows any material on the blades to fall into the bin and leaves the blade assemblies free to rotate back to the operative position shown in FIGS. 3, 8 and 12.

The blade assemblies are preferably moulded in plastics. A very small mass is required to cause rotation of the blade assemblies and the smooth surface of the elongate blades ensures a low coefficient to friction enabling lighter and smaller materials to slide off the inclined surfaces. A counterweight may be added to the blades of any embodiment to ensure correct rotation and positioning of the blade assemblies in operation. Providing adjustable counterweights allows the operator to finely balance the blade assemblies. The blades need not be of different lengths but may have the same length and rely on counterweights, springs, different weighted blades or shifting pivot points to cause rotation into the operative position. Nor do the blades need to be the shapes disclosed herein or separated at the angles disclosed herein, provided they are able to rotate as described above. In the above embodiments gravity works to allow disposed articles to slide from the displaced blades into the bin and also works to re-position the blade assemblies to be once more operative.

It is understood that the closure member can include a frame that is attached to the mouth of the bin or a cover that is attached to the mouth of the bin. The closure member may also be an integral part of the mouth of the bin, or an integral part of the cover attached to the mouth of the bin. It is further understood that one blade assembly may be supported by the bin and the other blade supported by the cover or frame.

Although it is not shown in the drawings, the frame 30, 130, 230 is designed in a manner that there is no access to the container from the periphery of the frame outside the blade assemblies. Thus to place contents into the bin they must be placed within the space defined by the upwardly extending blades with inturn ends 48, 148, 248 shown in FIGS. 3, 8, 11.

It will be understood to persons skilled in the art of the invention that many modifications may be made without departing from the spirit and scope of the invention.

Having now discussed my invention, what I claim is:

1. A closure member for a bin having an enclosure with a closed end and a mouth, the closure member being adapted to be secured to or to form part of the mouth of the bin and comprising two blade assemblies mounted to be rotatable and to extend across the mouth of the bin, means to urge each blade assembly to rotate to an operative position, each blade assembly comprising at least two mutually inclined blades extending radially from an axis, the blade assemblies being arranged so that adjacent blades of each assembly are vertically offset and overlap to define, in the operative position, a vertical gap between the adjacent blades.

2. The closure member according to claim 1 wherein the means to urge each blade assembly to rotate to an operative position is biasing means acting between the blade assembly and its mount.

3. The closure member according to claim 1 wherein each blade assembly is mounted in an unbalanced configuration to cause the blade assembly to rotate to the operative position.

4. The closure member according to claim 1 wherein each blade assembly is pivoted about a point offset from the center of gravity of the blade assembly to thereby urge the blade assembly towards the operative position.

5. The closure member according claim 1 wherein each blade assembly comprises three blades extending radially from the axis at substantially equal angular spacing.

6. The closure member according to claim 1 wherein the blades are of differing shape and length so that when the blade assembly is supported across the mouth of the bin about the axis the assembly is unbalanced to rotate to the operative position.

7. The closure member according to claim 1 wherein the blades are identical and a counterbalance weight is placed on at least one blade to unbalance the assembly to the operative position.

8. The closure member according to claim 1 wherein each blade assembly is positioned spaced apart with the pivot axis blade assembly is positioned spaced apart with the pivot axis of one assembly being vertically displaced from the pivot axis of the other assembly.

9. The closure member according to claim 1 wherein the closure member defines a stop for each blade assembly against which the assembly abuts to assume the operative position.

10. The closure member according to claim 1 wherein the overlapping blades of each assembly, when in the operative position, are downwardly inclined.

11. The closure member according to claim 1 wherein the blade assemblies are secured to the mouth of the bin.

12. The closure member according to claim 1 wherein the blade assemblies are secured to extend across a frame, the frame being adapted to fit with the mouth of the bin.

13. The closure member according to claim 1 wherein the blade assemblies are secured to a cover adapted to fit onto the mouth of the bin, the cover having a closable aperture to provide access to the bin.

14. The closure member according to claim 1 wherein the blades are interconnected by end flanges and the assembly is pivotally supported about a pivot axis through the end flanges.

15. The closure member according to claim 14 wherein the pivot axis is displaced from the center of gravity.

16. A bin having an enclosure with a closed end and a mouth end incorporating a closure member in accordance with claim 1.

17. A bin according to claim 16 wherein a cover is place over the mouth of the bin to cover the closure member and close off the bin.

18. A bin according to claim 17 wherein the cover is hinged to one side of the bin.

19. A bin according to claim 18 wherein as the cover is closed the underside of the cover rotates the blade assemblies to allow the cover to assume a latched configuration with the opposite side of the bin.

20. A bin having an enclosure with a closed end and a mouth, a removable cover adapted to fit over the mouth to close off the bin, and a closure member positioned to extend across the mouth of the bin, the closure member comprising two blade assemblies mounted to be rotatable and to extend across the mouth of the bin, means to urge each blade assembly to rotate to an operative position, each blade assembly comprising at least two mutually inclined blades extending radially from an axis, the blade assemblies being arranged so that adjacent blades of each assembly are vertically offset and overlap to define, in the operative position, a vertical gap between the adjacent blades.

21. The bin according to claim 20 wherein each blade assembly is mounted in an unbalanced configuration to cause the blade assembly to rotate to the operative position.

22. The bin according to claim 20 wherein the means to urge each blade assembly to rotate to an operative position comprises biasing means acting between the blade assembly and its mount.

23. A closure member for a bin having an enclosure with a closed end and a mouth, the closure member being adapted to be secured to or to form part of the mouth of the bin and comprising two blade assemblies mounted to be rotatable and to extend across the mouth of the bin, each blade assembly being pivoted about a point offset from the center of gravity of the blade assembly to render the blade assembly unbalanced to thereby urge the blade assembly to rotate to the operative position, each blade assembly comprising at least one blade, the blade assemblies being arranged so that adjacent blades of each assembly are vertically offset and overlap to define, in the operative position, a vertical gap between the adjacent blades.

* * * * *